US009126157B2

(12) United States Patent
Itoh

(10) Patent No.: US 9,126,157 B2
(45) Date of Patent: Sep. 8, 2015

(54) STIRRING DEVICE AND STIRRING METHOD

(71) Applicant: AOI SEIKI, CO., LTD., Kumamoto-shi, Kumamoto-ken (JP)

(72) Inventor: Teruaki Itoh, Kumamoto (JP)

(73) Assignee: AOI SEIKI CO., LTD., Kumamoto-Shi, Kumamoto-Ken (JP)

( * ) Notice: Subject to any disclaimer, the term of this patent is extended or adjusted under 35 U.S.C. 154(b) by 0 days.

(21) Appl. No.: 14/031,220

(22) Filed: Sep. 19, 2013

(65) Prior Publication Data

US 2014/0086004 A1    Mar. 27, 2014

(30) Foreign Application Priority Data

Sep. 21, 2012  (JP) ................................. 2012-208305
Nov. 21, 2012  (JP) ................................. 2012-255721

(51) Int. Cl.

| B01F 9/10 | (2006.01) |
|---|---|
| G01N 35/02 | (2006.01) |
| B01F 9/00 | (2006.01) |
| B01F 13/10 | (2006.01) |
| B01F 15/00 | (2006.01) |
| G01N 35/00 | (2006.01) |

(52) U.S. Cl.
CPC .............. B01F 9/0016 (2013.01); B01F 9/003 (2013.01); B01F 9/0014 (2013.01); B01F 9/10 (2013.01); B01F 13/1072 (2013.01); B01F 15/00253 (2013.01); B01F 15/00318 (2013.01); *G01N 2035/00524* (2013.01)

(58) Field of Classification Search
None
See application file for complete search history.

(56) References Cited

U.S. PATENT DOCUMENTS

| 3,722,790 | A | * | 3/1973 | Natelson ......................... 494/11 |
|---|---|---|---|---|
| 4,895,453 | A | * | 1/1990 | Devlin et al. ................. 366/219 |
| 5,472,669 | A | * | 12/1995 | Miki et al. ....................... 422/63 |
| 5,637,275 | A | * | 6/1997 | Carey et al. ..................... 422/64 |
| 6,081,326 | A | * | 6/2000 | Rousseau et al. ............. 356/246 |
| 6,299,567 | B1 | * | 10/2001 | Forrest et al. .................. 482/64 |
| 6,358,471 | B1 | * | 3/2002 | Ishihara .......................... 422/65 |
| 2001/0000353 | A1 |  | 4/2001 | Hoshiba et al. |
| 2004/0095845 | A1 | * | 5/2004 | Peterman, Jr. ................ 366/213 |
| 2007/0000352 | A1 | * | 1/2007 | Itoh ................................. 81/3.2 |
| 2008/0190735 | A1 | * | 8/2008 | Luoma .......................... 198/340 |
| 2010/0226828 | A1 |  | 9/2010 | Itoh |
| 2010/0286603 | A1 | * | 11/2010 | Winderstrom .................. 604/68 |
| 2011/0053169 | A1 | * | 3/2011 | Macioszek et al. ............... 435/6 |

(Continued)

FOREIGN PATENT DOCUMENTS

| CA | 2 738 140 | 1/2012 |
|---|---|---|
| CN | 1689958 | 11/2005 |

(Continued)

OTHER PUBLICATIONS

Extended European Search Report in EP 13 00 4575 dated Jan. 7, 2014.

(Continued)

*Primary Examiner* — Jill Warden
*Assistant Examiner* — Benjamin Whatley
(74) *Attorney, Agent, or Firm* — Nixon & Vanderhye P.C.

(57) ABSTRACT

A stirring device according to an aspect is provided with a holder which holds a specimen container accommodating a specimen in an upright position and a rotation mechanism section configured to rotate the specimen container, thereby stirring the specimen therein.

2 Claims, 2 Drawing Sheets

(56) References Cited

U.S. PATENT DOCUMENTS

| | | |
|---|---|---|
| 2011/0174708 A1 | 7/2011 | Oota et al. |
| 2012/0107197 A1* | 5/2012 | Luethi et al. ............ 422/561 |
| 2014/0086004 A1 | 3/2014 | Itoh |
| 2014/0086808 A1 | 3/2014 | Itoh |

FOREIGN PATENT DOCUMENTS

| | | |
|---|---|---|
| CN | 101823010 | 9/2010 |
| CN | 102171575 | 8/2011 |
| CN | 102413806 | 4/2012 |
| DE | 199 12 496 | 9/1999 |
| EP | 0 435 481 A2 | 7/1991 |
| EP | 2 711 072 | 3/2014 |
| JP | 2010202269 A * | 9/2010 |
| TW | 405442 | 3/1997 |
| WO | WO 2010/101151 A1 | 9/2010 |
| WO | WO 2010/128394 A2 | 11/2010 |

OTHER PUBLICATIONS

Canadian Office Action dated Oct. 15, 2014 issued in Canadian Patent Application No. 2,827,624, 3 pp.
Chinese Office Action mailed Jun. 3, 2015 in Chinese Patent Application No. 201310426010.7 and English Translation, 18 pp.
Taiwanese Office Action mailed May 27, 2015 in Taiwanese Patent Application No. 102133533 and English Translation, 9 pp.

* cited by examiner

STIRRING DEVICE AND STIRRING METHOD

CROSS-REFERENCE TO RELATED APPLICATIONS

This application is based upon and claims the benefit of priority from the prior Japanese Patent Applications No. 2012-208305, filed Sep. 21; and No. 2012-255721, filed Nov. 21, the entire contents of which are incorporated herein by reference.

BACKGROUND OF THE INVENTION

1. Field of the Invention

The present invention relates to a stirring device and stirring method.

2. Description of the Related Art

In some tests, such as sediment, qualitative, and biochemical tests, urine samples and other specimens are stirred before they are aliquoted and dispensed, in order to avoid the influence of precipitation of their ingredients. In general, a specimen is agitated manually or by using a dropper or other rod-like tool. Also, an automatic stirring device has been investigated that is configured to stir a specimen by sucking in and discharging it by means of tips.

In the manual stirring method described above, a human operator's skill affects the stirring accuracy, thus it is difficult to achieve a high degree of stirring accuracy. In the stirring method based on suction and discharge, on the other hand, the positional relationship between the tips, suction rate, and other conditions affect the stirring accuracy, thus it is hard to entirely accurately stir the specimen in a specimen container.

BRIEF SUMMARY OF THE INVENTION

A stirring device according to an embodiment comprises a holder which holds a specimen container accommodating a specimen in an upright position and a rotation mechanism section configured to rotate the specimen container, thereby stirring the specimen therein.

According to the embodiment, high-accuracy stirring can be performed with a simple structure.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
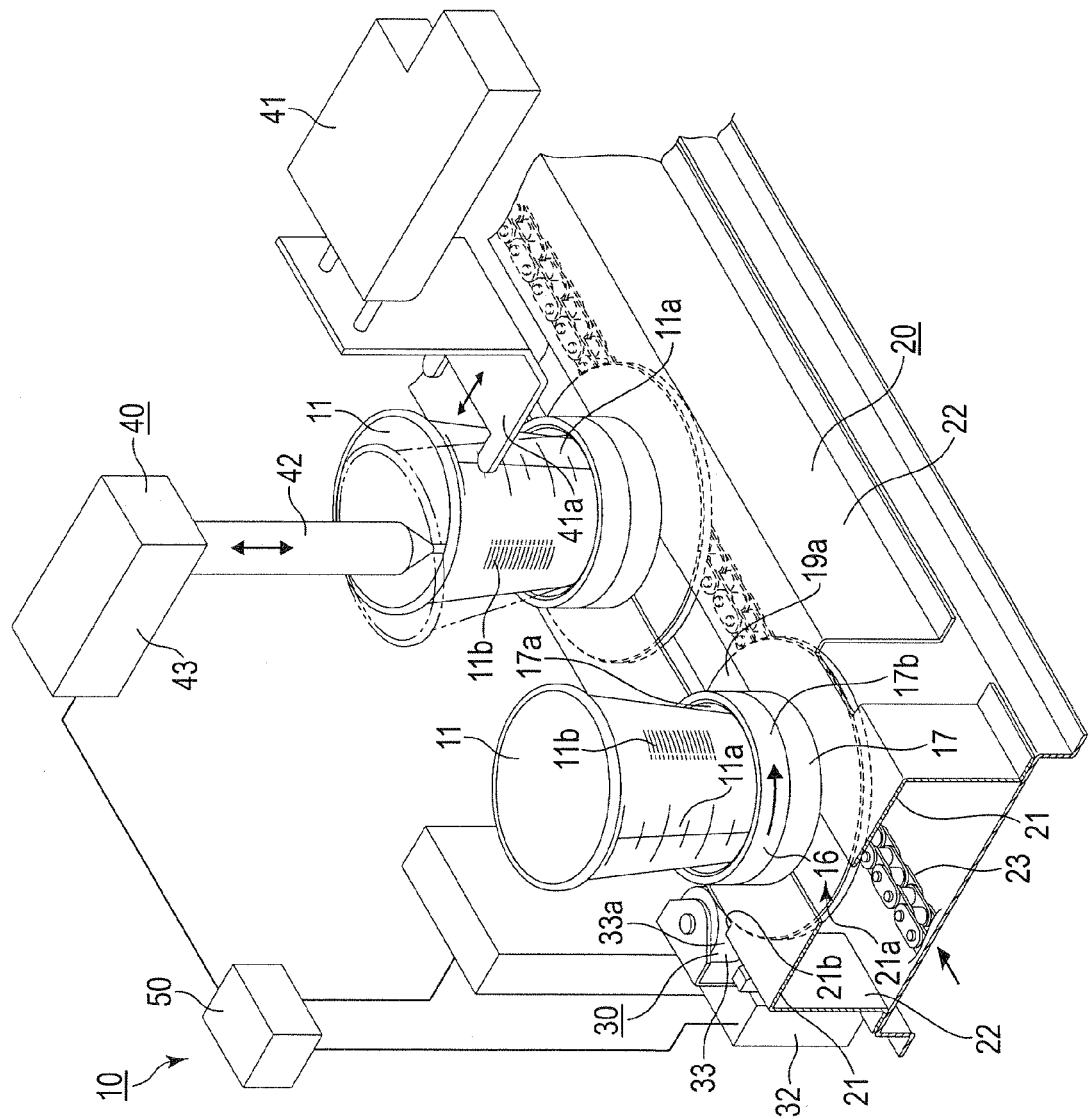
FIG. 1 is an explanatory diagram of a specimen processing apparatus according to a first embodiment of the invention.
Figure 2:
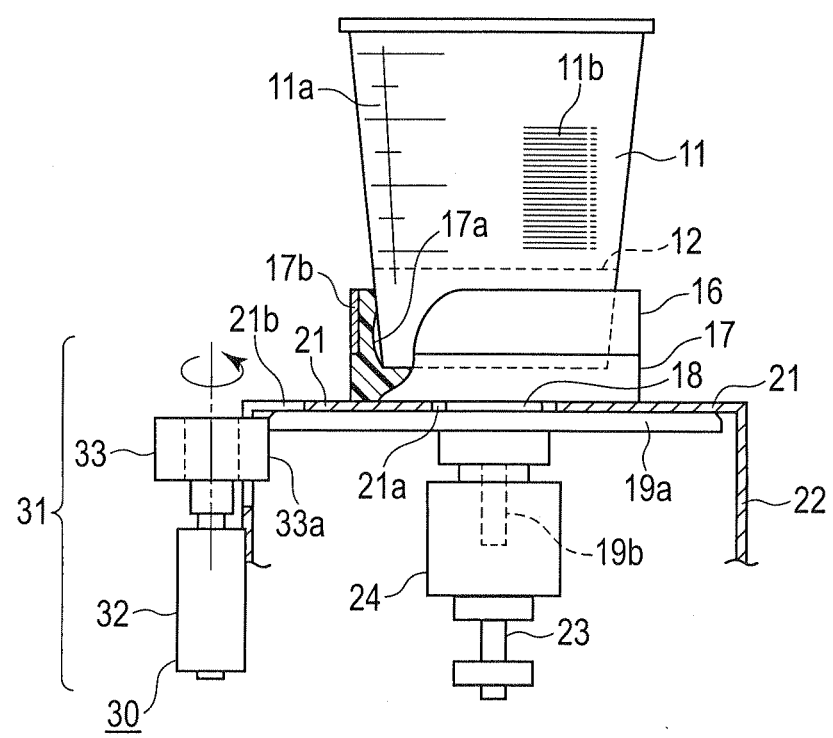
FIG. 2 is a cutaway side view of a stirring unit according to the embodiment.

A specimen processing apparatus 10 according to a first embodiment of the present invention will now be described with reference to FIGS. 1 and 2. FIG. 1 is an explanatory diagram of the specimen processing apparatus 10 of the present embodiment, and FIG. 2 is a cutaway side view of a stirring unit 30 and shows, partially in section, a frame 22 and the like. In each of these drawings, configurations are enlarged, reduced, or omitted as required for ease of explanation. In these drawings, arrows X, Y and Z individually indicate three orthogonal directions.

The specimen processing apparatus 10 is an apparatus that previously stirs, distributes, and dispenses a specimen prior to various inspection processes, and is used as, for example, a pre-treatment unit of an analyzer. The specimen processing apparatus 10 comprises a transport unit 20, the stirring unit (stirrer) 30, an aliquoting/dispensing unit 40, and a control unit 50. The transport unit 20 transports a cup 11 for use as a specimen container along a predetermined transport path. The stirring unit 30 is configured to rotate the transported cup 11 together with a holder 16, thereby stirring a specimen 12. The aliquoting/dispensing unit 40 distributes the specimen 12 from the cup 11 immediately after the stirring and dispenses it into a Spitz tube or the like. The control unit 50 controls the operations of the individual units. Further, various processing units are installed on the upstream and downstream sides of the transport path, whereby the transported cup 11 or the specimen therein is subjected to various steps of processing.

In the present embodiment, the specimen 12 is a urine sample and the cup 11 for use as the specimen container is cylindrical. For example, the cup 11 is an open-topped circular cylinder of paper having an internal space that accommodates the urine sample. The cup 11 is tapered from top to bottom and is supported and transported in an upright position with its lower part fitted in a holding portion 17 of the holder 16. Various specimen data, such as a scale 11a for gauging the amount of the specimen, barcode 11b representative of identification data on the specimen, etc., are displayed on the outer peripheral surface of the cup 11. In the present embodiment, the cup 11 has a bottom diameter of about 30 to 100 mm, top opening diameter of 50 to 150 mm, and height of 30 to 100 mm, for example.

As shown in FIGS. 1 and 2, the holder 16 integrally comprises the holding portion 17, neck portion 18, and large-diameter turntable 19, which are coaxial with one another. The holding portion 17 is configured to hold the outer surface of the lower part of the cup 11. The neck portion 18 is located continuously with the bottom of the holding portion 17. The turntable 19 adjoins the bottom of the neck portion 18.

The holding portion 17 is a bottomed circular cylinder the top side of which is expanded in diameter. The holding portion 17 comprises a cylindrical portion 17a and metallic outer layer 17b. The cylindrical portion 17a is a bottomed circular cylinder of resin. The outer layer 17b covers a part of the outer periphery of the cylindrical portion 17a. The cup 11 can be held in a substantially vertical upright position in a circular accommodation space, with the inner surface of the resin cylindrical portion 17a in close contact with the outer periphery of the cup 11.

The neck portion 18 is integrally molded so that it adjoins the bottom of the holding portion 17 and protrudes continuously downward from the center of the bottom of the holding portion 17. The neck portion 18 is guided along a slit 21a between guide rails 21 of the transport unit 20.

The turntable 19 comprises a disk portion 19a and engaging portion 19b. The disk portion 19a is a resin disk that adjoins the bottom of the neck portion 18. The engaging portion 19b protrudes downward from the center of the disk portion 19a. The outer peripheral surface of the disk portion 19a is disposed in contact with that of a roller 33 and configured to rotate following the roller 33 under friction.

The engaging portion 19b projects downward along the axis of rotation and is rotatably engaged with and held by a supporting portion 24 on a chain belt 23 of the transport unit 20.

The transport unit 20 is a chain conveyor system comprising the frame 22, chain belt 23, supporting portion 24, and transport motor, and has the function of transporting the holder 16 along the predetermined transport path. The frame 22 comprises a pair of guide rails 21 extending along the transport path. The chain belt 23 is disposed along the transport path and moves in engagement with the holder 16 below the guide rails 21. The supporting portion 24 supports the holder 16 on the chain belt 23. The transport motor serves to feed-drive the chain belt 23.

The slit 21a that defines the transport path is formed between the pair of guide rails 21. Further, one of the guide rails 21 comprises a window portion 21b that is formed by partially cutting off its lateral portion where the roller 33 and turntable 19 face each other. The roller 33 is exposed through the window portion 21b.

The turntable 19 is disposed below the pair of guide rails 21, and the holding portion 17 above the guide rails 21. The holder 16 is anchored to the frame 22 with its neck portion 18 allowed to move guided by the slit 21a between the guide rails 21. Below the turntable 19, moreover, the engaging portion 19b is engaged with and held by the supporting portion 24 on the chain belt 23.

The stirring unit 30 comprises a rotation mechanism section 31 configured to rotate the holder 16 that holds the cup 11, in which the specimen 12 is accommodated, in an upright position. The rotation mechanism section 31 comprises a stirring motor 32 controlled by the control unit 50 and the roller 33 connected to the motor 32 for rotation. In this arrangement, the disk portion 19a of the holder 16 that rotates following the rotation of the roller 33 serves as a part of the power transmission function of the rotation mechanism section 31.

The roller 33 is a circular cylinder of resin. The roller 33 functions as a power transmission system that is rotated by the stirring motor 32 and rotates the disk portion 19a in contact with its outer peripheral surface of resin.

As shown in FIG. 1, a barcode reader 34 is provided beside the stirring unit 30. The barcode reader 34 detects the barcode 11b attached to the side of the cup 11, thereby detecting various displayed data, in the initial stage of rotation of the cup 11 during the stirring operation.

The aliquoting/dispensing unit 40 is located downstream adjacent to the stirring unit 30 in the transport path. The aliquoting/dispensing unit 40 comprises a tilting unit 41, nozzle 42, moving arm 43, and drive unit. The tilting unit 41 tilts the cup 11 after the stirring, for example. The nozzle 42 distributes and dispenses the specimen 12 in the cup 11. The moving arm 43 supports and activates the nozzle 42. The drive unit actuates the moving arm 43 and nozzle 42. The aliquoting/dispensing unit 40 operates at a predetermined timing under the control of the control unit 50.

The tilting unit 41 comprises a pressing piece 41a capable of advancing and retreating. The tilting unit 41 advances or retreats the pressing piece 41a at a predetermined timing under the control of the control unit 50, thereby pressing a predetermined position on the side of the cup 11 to a predetermined angle immediately after the stirring so that the cup 11 is tilted.

The nozzle 42 is configured so that it can suck in and discharge a predetermined amount of the specimen 12 and can move up and down (or advance and retreat). The nozzle 42 is movable as the moving arm 43 is operated under the control of the control unit 50.

The following is a description of the operation of the specimen processing apparatus 10 according to the present embodiment.

The transport motor is driven by the control unit 50 to run the chain belt 23 with the holder 16 rotatably supported by the frame 22 in the transport unit 20. As the chain belt 23 runs in this manner, the holder 16 moves in an upright position along the transport path.

The cups 11 are held at the predetermined intervals in the transport path and sequentially flow as the chain belt 23 is run. Thus, the cups 11 can be simultaneously subjected to various steps of processing. Stirring and aliquoting/dispensing processes will now be successively described in connection with one of the cups 11.

When the subject cup 11 reaches the processing station of the stirring unit 30, the control unit 50 suspends the movement of the chain belt 23. Then, the roller 33 is rotated by driving the stirring motor 32. If the roller 33 rotates with its outer peripheral surface 33a in contact with the resin surface of the disk portion 19a of the turntable 19, friction urges the turntable 19 to rotate following the rotation of the roller 33. Thereupon, the holder 16 rotates, and the cup 11 held in the holder 16 rotates in an upright position.

By this rotation, the specimen 12 in the cup 11 is entirely stirred. The rotational speed, time conditions, etc., are determined according to the amount of the specimen 12 and the like, and are set so as to, for example, prevent scattering and achieve a desired stirring accuracy. In the present embodiment, the rotational speed is set to, for example, about 150 to 200 rpm.

In the present embodiment, the barcode reader 34 detects the barcode 11b attached to the side of the cup 11, thereby detecting the various displayed data, while the cup 11 is rotating. Specifically, a reading operation is efficiently performed by detecting the barcode 11b on the side of the stirring cup 11 based on the rotary motion of the cup 11.

After the stirring process, the transport unit 20 is driven to deliver the cup 11 to the aliquoting/dispensing unit 40 on the downstream side. When the subject cup 11 reaches the processing station of the aliquoting/dispensing unit 40, the operation is suspended. Another cup 11 is delivered to the stirring unit 30 and subjected to the same stirring process as described above.

In the aliquoting/dispensing unit 40, the moving arm 43 is driven by the control unit 50 to move the nozzle 42 to the space just above the cup 11.

A tilting operation is performed to tilt the cup 11 such that a predetermined portion of the cup 11 is pressed to a predetermined angle by the tilting unit 41 while the nozzle 42 is moving. If the cup 11 is tilted, the specimen 12 therein collects in the position of the nozzle 42 and its depth becomes so great that it can be easily distributed.

Then, the nozzle 42 is lowered at a predetermined timing and fitted into the tilted cup 11 after the stirring. In this fitted state, a suction operation is performed and a predetermined amount of the specimen 12 in the cup 11 is distributed.

After the distribution, the nozzle 42 is raised to be removed from the cup 11 and is moved to a predetermined dispensing point by the moving arm 43. Then, the specimen 12 is discharged and dispensed into another container, such as a Spitz tube. In this way, the stirring and aliquoting/dispensing processes are completed.

After the end of the stirring process, the pressing piece 41a of the tilting unit 41 is retracted to restore the cup 11 to the upright position, and the transport unit 20 is driven at a predetermined timing to deliver the cup 11 downward. When this is done, another cup 11 having undergone the stirring process on the upstream side is delivered to the aliquoting/dispensing unit 40. A plurality of cups 11 are sequentially processed by repeating these processes.

According to the specimen processing apparatus 10 and stirring unit 30 of the present embodiment, the stirring process can be easily performed accurately merely by rotating the holder 16 that supports the cup 11. Specifically, the specimen 12 can be entirely uniformly stirred merely by rotating the cup 11 together with the holder 16 immediately before the aliquoting/dispensing process. According to this method, compared with a method in which the specimen 12 is agitated by means of a tool introduced therein or a method by which the specimen 12 is stirred by being sucked in and discharged, the specimen 12 can be stirred more thoroughly, so that the stirring accuracy is improved.

Further, the specimen 12 can be stirred in a non-contact manner, that is, without direct contact, so that contamination can be prevented and a high level of hygiene can be achieved. In the case where the specimen is directly stirred by a stirrer or other tool introduced into the container, the tool requires replacement and is awkward to handle. According to the present embodiment, however, processing can be performed quickly and efficiently with a simple structure by virtue of not using such a tool.

The present invention is not limited directly to the embodiments described herein, and in carrying out the invention, its constituent elements may be embodied in modified forms without departing from the scope or spirit of the invention. Although a urine sample and cup are given as examples of the specimen and specimen container, respectively, according to the embodiments, for example, the invention is also applicable to other specimens and specimen containers.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A stirring device comprising:
a holder which tiltably holds a specimen container accommodating a specimen in an upright position;
a rotation mechanism section configured to rotate the specimen container, thereby stirring the specimen therein, wherein the rotation mechanism section comprises a motor, a roller which is connected to an output shaft of the motor for rotation and has an outer surface of a friction material containing a resin, and a turntable provided on the holder and configured to contact an outer surface of the roller and rotate following the rotation of the roller, and wherein the specimen container is a cylindrical cup accommodating the specimen and configured to rotate while holding the cup in an upright position; and
a tilting unit disposed downstream of the rotation mechanism section, the tilting unit including a pressing piece that is disposed above the holder and is advanced into and retreated from a path of the holder to directly press the specimen container without tilting the holder.

2. A stirring method comprising:
holding with a holder a specimen container accommodating a specimen in an upright position;
rotating the specimen container with a rotation mechanism section, thereby stirring the specimen therein;
tilting with a tilting unit the specimen container for a downstream processing,
wherein the rotation mechanism section comprises a motor, a roller which is connected to an output shaft of the motor for rotation and has an outer surface of a friction material containing a resin, and a turntable provided on the holder, wherein the rotating step is practiced by contacting the turntable with an outer surface of the roller to rotate the turntable following the rotation of the roller, wherein the specimen container is a cylindrical cup accommodating the specimen, and wherein the rotating step is further practiced by rotating the specimen cup while holding the cup in an upright position, and
wherein the tilting step is practiced by advancing and retreating from a path of the holder a pressing piece of the tilting unit that is disposed downstream of the rotation mechanism section and above the holder to directly press the specimen container without tilting the holder.

* * * * *